US012797378B2

(12) United States Patent
Polymeropoulos et al.

(10) Patent No.: US 12,797,378 B2
(45) Date of Patent: Nov. 17, 2026

(54) USE OF TRADIPITANT IN MOTION SICKNESS

(71) Applicant: Vanda Pharmaceuticals Inc., Washington, DC (US)

(72) Inventors: Mihael H. Polymeropoulos, Potomac, MD (US); Vasilios Polymeropoulos, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 334 days.

(21) Appl. No.: 18/595,134

(22) Filed: Mar. 4, 2024

(65) Prior Publication Data

US 2024/0299373 A1 Sep. 12, 2024

Related U.S. Application Data

(60) Provisional application No. 63/488,549, filed on Mar. 6, 2023.

(51) Int. Cl.

*C07D 401/14* (2006.01)
*A61K 9/00* (2006.01)
*A61K 9/48* (2006.01)
*A61K 31/444* (2006.01)
*A61P 1/08* (2006.01)

(52) U.S. Cl.

CPC .......... *A61K 31/444* (2013.01); *A61K 9/0053* (2013.01); *A61K 9/4825* (2013.01); *A61P 1/08* (2018.01)

(58) Field of Classification Search

CPC ........ C07D 401/14; A61K 31/444; A61P 1/08
See application file for complete search history.

(56) References Cited

U.S. PATENT DOCUMENTS

| | | | |
|---|---|---|---|
| 5,585,385 | A | 12/1996 | Natsugari et al. |
| 6,140,324 | A | 10/2000 | Tattersall |
| 6,297,375 | B1 | 10/2001 | Bos et al. |
| 7,176,205 | B2 | 2/2007 | Hoffmann et al. |
| 7,179,804 | B2 | 2/2007 | Amegadzie et al. |
| 7,381,826 | B2 | 6/2008 | Borghese |
| 7,799,782 | B2 | 9/2010 | Munson |
| 8,772,496 | B2 | 7/2014 | Chen |
| 10,463,655 | B2 | 11/2019 | Polymeropoulos et al. |
| 10,772,880 | B2 | 9/2020 | Polymeropoulos et al. |
| 10,821,099 | B2 | 11/2020 | Polymeropoulos et al. |
| 11,324,735 | B2 | 5/2022 | Polymeropoulos et al. |
| 11,549,147 | B2 | 1/2023 | Polymeropoulos et al. |
| 2014/0378521 | A1 | 12/2014 | Zhang et al. |
| 2015/0320866 | A1 | 11/2015 | Ottoboni et al. |
| 2016/0024092 | A1 | 1/2016 | Wan et al. |
| 2016/0136162 | A1 | 5/2016 | Trento et al. |
| 2020/0030307 | A1 | 1/2020 | Polymeropoulos et al. |

FOREIGN PATENT DOCUMENTS

| | | | |
|---|---|---|---|
| JP | 2006199614 | A | 8/2006 |
| JP | 2014193155 | A | 10/2014 |
| WO | 03011860 | A2 | 2/2003 |
| WO | 2007096782 | A2 | 8/2007 |
| WO | 2014209962 | A1 | 12/2014 |

OTHER PUBLICATIONS

Conder G.A. et al, "Efficacy and safety of maropitant, a selective neurokinin 1 receptor antagonist, in two randomized clinical trials for prevention of vomiting due to motion sickness in dogs," J Vet Pharmacy Ther., v. 31, pp. 528-532 (2008).

Yamamoto, Nobuharu et al., Effect of a novel NK1 receptor antagonist, fosaprepitant (Proemend®), used in patients with oral cancer treated with cisplatin, Oral Tumors 25(3): 109-114 (2013).

R. Saito, et al, The role of tachykinin NK-1 receptors in emetic action in the area postrema of ferrets, Folia Pharmacol. Jpn. (Nippon Yakurigaku Zasshi) 114, Suppl 1, 209P-214P (1999).

Director of New Drugs Division, Pharmaceutical Affairs Bureau, Ministry of Health and Welfare, General Guidelines for Clinical Evaluation of New Drugs, No. 43, addressed to the Chiefs of Health Administration Departments in each prefecture (Jun. 29, 1992).

Notice of Reasons for Rejection for JP Application No. 2021-12356, Mailing No. 083985, mailed Sep. 17, 2024.

Anonymous, "History of Changes for Study: NCT01919944: Study of Itch Control by VLY-686 in Healthy Volunteers After Intradermal Injections of Substance P," U.S. National Library of Medicine, ClinicalTrials.gov archive, retrieved from: https://clinicaltrials.gov/ct2/history/NCT01919944?A=5&B=5&C=merged on Dec. 16, 2019, 9 pages.

Anonymous, "History of Changes for Study: NCT02004041: Proof of Concept of VLY-686 in Subjects With Treatment-Resistant Pruritus Associated with Atopic Dermatitis," U.S. National Library of Medicine, ClinicalTrials.gov archive, retrieved from: https://clinicaltrials.gov/ct2/history/NCT02004041?A=4&B=4&C=merged on Dec. 16, 2019, 9 pages.

David G. Warr et al., Evaluation of risk factors predictive of nausea and vomiting with current standard-of-care antiemetic treatment: analysis of phase 3 trial of aprepitant in patients receiving adriamycin-cyclophosphamide-based chemotherapy: Supportive Care in Cancer, Springer-Verlag, vol. 19, No. 6, May 13, 2010, pp. 807-813. (XP019896207).

FDA; "Guidence for Industry Exposure-Response Relationships—Study Design, Data Analysis, and Regulatory Applications;" Apr. 2003; pp. 1-28.

George et al., "Neurokinin 1 Receptor Antagonism as a Possible Therapy for Alcoholism;" Science, vol. 319, No. 2869, Mar. 14, 2008, 6 pages.

(Continued)

*Primary Examiner* — Brenda L Coleman
(74) *Attorney, Agent, or Firm* — Hoffman Warnick LLC

(57) ABSTRACT

Disclosed herein is an improved method of treating or preventing motion sickness or at least one symptom thereof, comprising treatment with the NK-1 receptor antagonist, tradipitant based on ethnicity of the individual to be treated.

20 Claims, 6 Drawing Sheets

(56) References Cited

OTHER PUBLICATIONS

George et al., "Supporting Online Material for Neurokinin 1 Receptor Antagonism as a Possible Therapy for Alcoholism," Science, vol. 319, No. 2869, Mar. 14, 2008, 14 pages.

Pasricha Pankaj J. et al., "Aprepitant Has Mixed Effects on Nausea and Reduces Other Symptoms in Patients with Gastroparesis and Related Disorders," Gastroenterology: Official Publication of The American Gastroenterological Association, Williams & Wilkins, US, vol. 154, No. 1, Oct. 28, 2017, p. 65. (XP085311721).

Sadick Research Group; "Tradipitant in Treatment-Resistant Pruritus Associated With Atopic Dermatitis;" ClinicalTrials.gov Identifier NCT02672410; First Received Feb. 1, 2016; last Updated Feb. 2, 2016; accessed on Feb. 11, 2016; p. 3; <https://clinicaltrials.gov/ct2/show/study/NCT02672410?TERM=TRADIPITANT&RANK=3>.

Santini, "Aprepitant for management of severe pruritus related to biological cancer treatments: a pilot study," The Lancet; vol. 13; Oct. 2012; Published online Sep. 18, 2012; pp. 1020-1024.

Stander et al., "Targeting the Neurokinin Receptor 1 with Aprepitant: A Novel Antipruritic Strategy," PLOS ONE, vol. 6., No. 6, Jan. 1, 2010, 6 pages.

Sun et al., "Particle Size Specifications for Solid Oral Dosage Forms: A Regulatory Perspective;" American Pharmaceutical Review, Published May 1, 2010; pp. 1-9.

Tauscher et al., "Development of the 2nd generation neurokinin-1 receptor antagonist LY686017 for social anxiety disorder;" European Neuropsychopharmacology; 2010; Elsevier Science Publishers BV, Amsterdam, NL, vol. 20, No. 2, Feb. 1, 2010, 8 pages.

Trower, "Neurokinin-1 receptor antagonist orvepitant is an effective inhibitor of itch-associated response in a Mongolian gerbil model of scratching behaviour," Experimental Dermatology; 2014; 23, pp. 853-864.

Hagiwara, D. "Discovery of Low-Molecular Weight Antagonists of Substance P: Recent Developments and Prospects as a Therapeutic Agent," Journal of Synthetic Organic Chemistry, vol. 52, Issue 5, 1994, pp. 445-452.

Yates, B.J. et al. "Physiological basis and pharmacology of motion sickness: an update." Brain Research Bulletin, vol. 47, Issue 5, Nov. 15, 1998, pp. 395-406.

Cheung, B.S. et al. "Investigation of anti-motion sickness drugs in the squirrel monkey." NASA Technical Reports Server (NTRS), Journal of Clinical Pharmacology, vol. 32, Issue 2, Feb. 1, 1992.

Hickman, MA, et al., Safety, pharmacokinetics and use of the novel NK-1 receptor antagonist maropitant (Cerenia™) for the prevention of emesis and motion sickness in cats, J. Vet. Pharmacol. Therap. 31, 220-229 (May 8, 2008).

Lucot, JB et al., The effect of CP-99994 on the responses to provocative motion in the cat, Br J Pharmacol 120(1): 116-120 (1997).

Miller, G. "Tackling Alcoholism With Drugs." Science, Apr. 11, 2008, vol. 320, No. 5873, pp. 168-170.

Sinha, R. et al. "Translational and reverse translational research on the role of stress in drugs craving and relapse." Psychopharmacology, Apr. 15, 2011, vol. 218, No. 1, p. 69-82.

Kraus, Bonnie L. Hay. "Spotlight on the Perioperative Use of Maropitant Citrate." Veterinary Medicine: Research and Reports, 2017:8, pp. 41-51.

Reversal of NK-1 agonist-induced foot-tapping behavior in gerbils by tradipitant and competitor NK-1 antagonists: dose response

* = $p < 0.05$ vs. vehicle

Aprepitant ($ED_{50}$ = 0.4 ± 0.05 mg/kg, n=4-10, 1 hr.)

CP-122721 ($ED_{50}$ = 2.2 ± 0.5 mg/kg, n=6-8, 0.5 hr.)

Tradipitant ($ED_{50}$ = 0.03 ± 0.004 mg/kg, n=6-7, 2 hrs.)

Reversal of NK-1 agonist-induced foot-tapping behavior in gerbils by tradipitant and competitor NK-1 antagonists: Time course (p.o.; n=5-13)

Effect of tradipitant on NK-1 agonist (GR73632)-induced vocalization in guinea pigs: tradipitant concentration range of 0.05 – 10 mg/kg Vehicle = CMC Duration of activity: suppression by tradipitant (0.1 mg/kg) of NK-1 agonist (GR73632)-induced vocalization in guinea pigs Vehicle = 10% ethanol/emulphor, 10%propylene glycol

USE OF TRADIPITANT IN MOTION SICKNESS

CROSS REFERENCE TO RELATED APPLICATIONS

The present patent application claims priority to US Provisional Patent Application No. 63/488,549, filed Mar. 6, 2023, which is incorporated by reference as though fully set forth herein.

BACKGROUND

The application relates generally to use of the NK-1 antagonist, tradipitant, for the treatment of motion sickness. More particularly, the application relates to improved treatment methods based on the ethnicity of the individual being treated.

Motion sickness is a disorder defined by a constellation of symptoms that can result from real or perceived sickness-inducing motion. Such motion may include, e.g., motion involving the head of an individual that can produce one or more symptoms characteristic of motion sickness. The sickness-inducing motion that gives rise to motion sickness may commonly include riding in any form of transportation such as, e.g., automobiles, buses, trains, other ground or rail transportation, boats under power, ferries, cruise ships, sailboats, personal water craft, canoes, kayaks, row boats, airplanes and helicopters, amusement rides, and certain gymnastic maneuvers such as somersaults. The symptoms of motion sickness typically can include, but are not limited to, nausea, vomiting, dizziness, headache, fullness, cold sweats, sweating, pallor, disorientation, and anorexia. Motion sickness has been reported to affect up to 30% of the general population under ordinary travel conditions that include sea, air, and land travel. The prevalence of motion sickness in one epidemiological study during bus travel found 28% of passengers reporting feeling ill while 13% reported experiencing nausea.

Under the sensory conflict theory, motion sickness is described as arising due to a mismatch between the perceptions of motion, or lack thereof, by the visual, vestibular, and somatosensory systems. A discrepancy between actual body position and perceived body position is believed to trigger the maladaptive response of motion sickness. Motion sickness is one of the most prevalent episodic disorders in the world, and its prevalence has dramatically increased with world population mobility. Despite the increasing prevalence of the disorder, the treatments available today, which are primarily antihistamines and anticholinergics, were first discovered in the 1940's. Currently, available therapies are not effective for all patients, and some of the medications used have significant side effect profiles.

The mammalian tachykinins (neurokinins [NKs]) are a family of peptide neurotransmitters that share a common C-terminal sequence. This group includes substance P (SP), neurokinin-A (NKA), and neurokinin-B (NKB). SP, the most abundant NK, preferentially binds to the neurokinin type-1 (NK-1) receptor and is involved in the regulation of many physiological processes. NK-1 receptors have been mapped in the central nervous system and were found to have a broad distribution in the brain, including the midbrain, basal ganglia, hypothalamus, and limbic system. Neurokinin receptors are also widely distributed in the gut, the bronchial tree, and the vascular system.

The NK-1 receptor has been identified as a potential therapeutic target for the treatment of motion sickness.

Maropitant, another neurokinin 1 receptor antagonist, is approved for the prevention of vomiting due to motion sickness in dogs and cats. A crossover study showed that the therapy reduced the occurrence of vomiting in over 75% of dogs as compared to placebo. This data supports the exploration of the effects of NK-1 antagonists on motion sickness in humans, though maropitant has a different molecular composition and pharmacokinetics from other NK-1 antagonists. Another NK1-receptor antagonist, aprepitant, is approved for postoperative nausea and vomiting (PONV) in adults, and for use with other medications in children and adults to prevent nausea and vomiting caused by certain anti-cancer (chemotherapy) medicines. Currently, tradipitant is being tested in clinical trials for the treatment of nausea and vomiting in patients with gastroparesis.

Tradipitant is a highly potent, selective, centrally penetrating, and orally active neurokinin-1 (NK-1) receptor antagonist, depicted below as the compound of Formula (I)

(I)

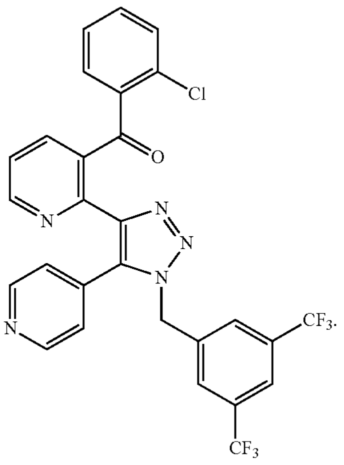

Tradipitant is disclosed in U.S. Pat. No. 7,320,994, and contains six main structural components: the 3,5-bis-trifluoromethylphenyl moiety, two pyridine rings, the triazol ring, the chlorophenyl ring, and the methanone. Tradipitant is known by the chemical names: 2-[1-[[3,5-bis(trifluoromethyl)phenyl]methyl]-5-(4-pyridinyl)-1H-1,2,3-triazol-4-yl]-3-pyridinyl](2-chlorophenyl)-methanone, and {2-[1-(3,5-bistrifluoromethylbenzyl)-5-pyridin-4-yl-1H-[1,2,3]triazol-4-yl]-pyridin-3-yl}-(2-chlorophenyl)-methanone, and has also been known as LY686017 and as VLY-686. Crystalline Forms IV and V of tradipitant are disclosed in U.S. Pat. No. 7,381,826, and a process for preparing crystalline {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV is disclosed in U.S. Pat. Nos. 8,772,496; 9,708,291; and 10,035,787.

In preclinical and clinical studies, tradipitant produces a long-lasting blockade of brain NK-1 receptors. Although the distinct pathways of nausea and vomiting are largely undetermined, a definitive role of SP acting at NK-1 receptors in the nucleus tractus solitarus has been confirmed. Previous clinical studies have demonstrated the efficacy of NK-1 antagonism in the prevention of chemotherapy induced and postoperative nausea and vomiting (CINV and PONV). U.S. Pat. No. 10,821,099 further describes the use of tradipitant in the treatment and prevention of motion sickness and symptoms thereof. U.S. Pat. No. 10,821,099 is incorporated by reference as though fully set forth herein.

BRIEF DESCRIPTION OF THE INVENTION

According to a first aspect of the disclosure, an improvement is provided for a method of treating an individual about to engage in an activity involving sickness-inducing motion. According to this aspect, the improvement comprises selecting the individual for treatment with tradipitant based on the ethnicity of the individual. In particular, the individual is selected based on the individual's Hispanic ethnicity. The improved method further comprises administering tradipitant to the selected individual, prior to the commencement of the activity, in an amount effective to prevent motion sickness or at least one symptom of motion sickness in the individual.

In certain embodiments, the activity is vehicle travel, e.g., via automobile, airplane, helicopter, boat, train, or bus.

In certain embodiments, the administration occurs about 30 minutes prior to entering a vehicle, and/or about 30 minutes prior to commencement of the vehicle travel.

In certain embodiments, the effective amount of tradipitant is about 100 to about 400 mg, about 100 to about 300 mg, about 100 to about 200 mg, about 150 to about 400 mg, about 150 to about 300 mg, about 150 to about 200 mg, about 170 mg, or 170 mg.

In certain embodiments, the improvement further comprises orally administering the tradipitant in the effective amount. The tradipitant may be orally administered in a solid immediate release form comprising tradipitant and one or more pharmaceutically acceptable excipients, and the solid immediate release form may be, e.g., a capsule or a tablet.

In certain embodiments, the at least one symptom may be nausea, vomiting, dizziness, headache, fullness, disorientation, or vomiting.

According to a second aspect of the disclosure, an improvement is provided for a method of treating an individual with motion sickness or at least one symptom thereof, comprising administering tradipitant to the individual at a dose that is effective to treat the motion sickness or a symptom thereof, wherein the dose effective to treat the motion sickness or the symptom thereof is determined based on an ethnicity of the individual. The dose is a first dose if the individual is Hispanic, and is a second dose if the individual is non-Hispanic.

In certain embodiments, the second dose is larger than the first dose.

In certain embodiments, the first dose is about 100 to about 400 mg, about 100 to about 300 mg, about 100 to about 200 mg, about 150 to about 400 mg, about 150 to about 300 mg, about 150 to about 200 mg, about 170 mg, or 170 mg. The second dose may be about 150 mg to about 600 mg, about 150 mg to about 450 mg, about 150 to about 300 mg, about 225 mg to about 600 mg, about 225 mg to about 450 mg, about 225 to about 300 mg, about 255 mg, or 255 mg.

In certain embodiments, the first dose is about 85 mg, or may be 85 mg; and the second dose is about 100 to about 400 mg, about 100 to about 300 mg, about 100 to about 200 mg, about 150 to about 400 mg, about 150 to about 300 mg, about 150 to about 200 mg, about 170 mg, or 170 mg.

In certain embodiments, the administering further comprises orally administering the tradipitant, which may be orally administered in a solid immediate release form comprising tradipitant and one or more pharmaceutically acceptable excipients. The solid immediate release form may be a tablet or a capsule.

In certain embodiments, the at least one symptom of motion sickness is nausea, vomiting, dizziness, headache, fullness, or disorientation.

According to a third aspect of the disclosure, a method is provided for treating an individual about to engage in an activity involving sickness-inducing motion, the method comprising: determining an effective dose of tradipitant for the individual, wherein the effective dose for the individual is a first dose if the individual is Hispanic, and is a second dose if the individual is non-Hispanic. The method further comprises administering the effective dose of tradipitant to the individual, prior to the commencement of the activity, whereby the effective dose is effective to prevent motion sickness or at least one symptom of motion sickness in the individual.

In certain embodiments, the second dose is larger than the first dose.

In certain embodiments, the second dose is about 100 to about 400 mg, about 100 to about 300 mg, about 100 to about 200 mg, about 150 to about 400 mg, about 150 to about 300 mg, about 150 to about 200 mg, about 170 mg, or is 170 mg; and the second dose is about 150 mg to about 600 mg, about 150 mg to about 450 mg, about 150 to about 300 mg, about 225 to about 600 mg, about 225 to about 450 mg, about 225 to about 300 mg, about 255 mg, or is 255 mg.

In other embodiments, the first dose is about 85 mg, or is 85 mg; and the second dose is about 100 to about 400 mg, about 100 to about 300 mg, about 100 to about 200 mg, about 150 to about 400 mg, about 150 to about 300 mg, about 150 to about 200 mg, about 170 mg, or is 170 mg.

In certain embodiments, the administering further comprises orally administering the tradipitant, which may be in a solid immediate release form comprising tradipitant and one or more pharmaceutically acceptable excipients. The solid immediate form may be, e.g., a capsule or a tablet.

In certain embodiments, the at least one symptom is nausea, vomiting, dizziness, headache, fullness, or disorientation.

According to a fourth aspect of the disclosure, tradipitant is provided for use in any of the preceding methods of treatment or improvements.

According to a fifth aspect of the disclosure, a pharmaceutical composition is provided comprising tradipitant for use in any of the preceding methods or improvements.

According to a sixth aspect of the disclosure, tradipitant is provided for use in the manufacture of a pharmaceutical composition. The pharmaceutical composition comprises tradipitant, and may be for use in any of the preceding methods or improvements.

These and other aspects, advantages and salient features of the invention will become apparent from the following detailed description, which, when taken in conjunction with the annexed figure(s) disclose embodiments of the invention.

Figure 1:
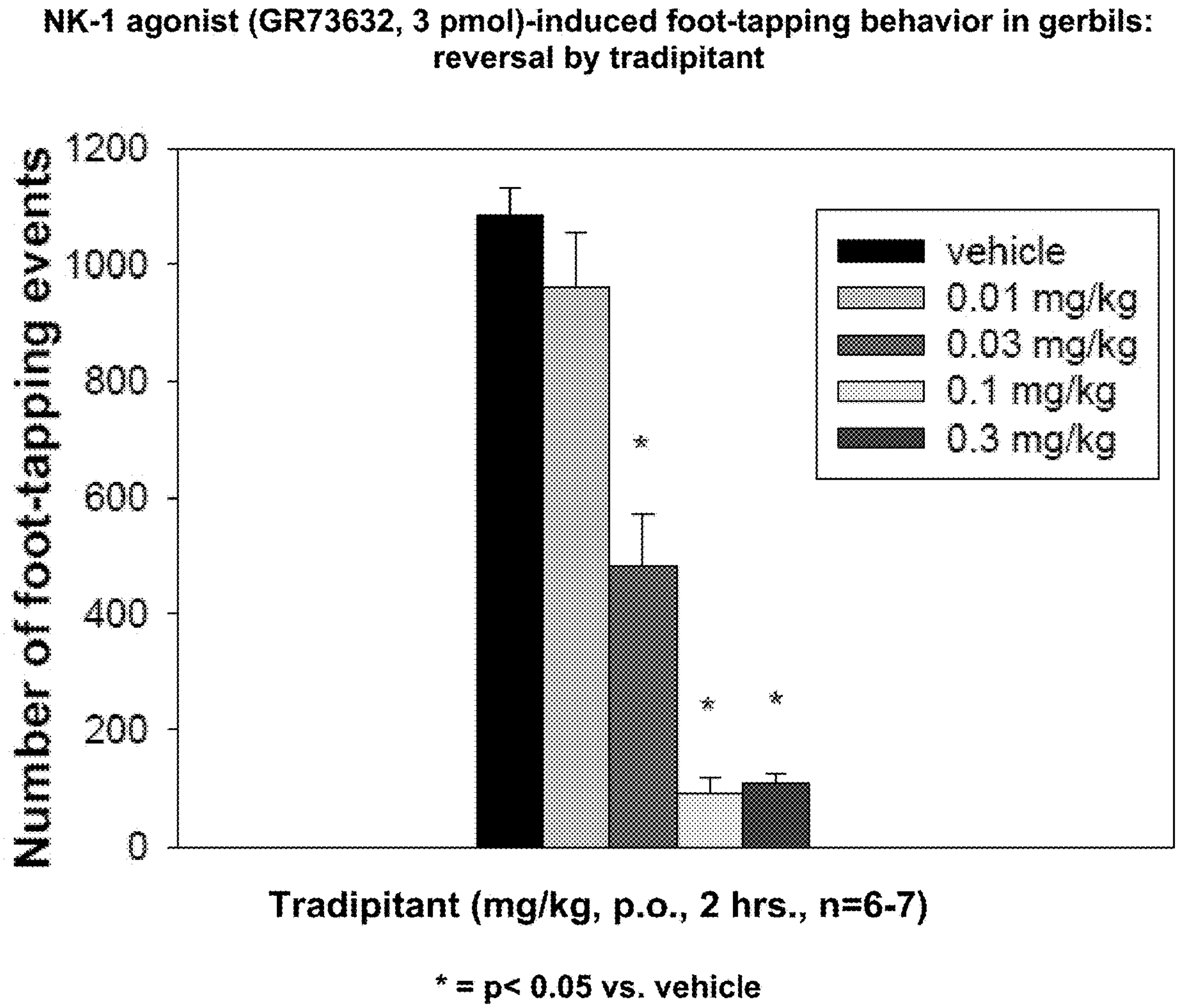
FIG. 1 illustrates the effect of tradipitant on NK-1 agonist (GR73632, 3 pmol, icv)-induced foot-tapping behavior after oral administration.

The drawings are intended to depict only typical aspects of the disclosure, and therefore should not be considered as limiting the scope of the disclosure.

DETAILED DESCRIPTION OF THE INVENTION

Improved methods are provided herein for treating an individual about to engage in an activity involving sickness-inducing motion, in order to treat, prevent, or ameliorate symptoms of motion sickness which may manifest in the individual as a result of the sickness-inducing motion as described herein. The methods include administration of the NK-1 antagonist, tradipitant, in an amount, i.e. at a dose that is effective to prevent or treat the motion sickness or the symptom(s) thereof in the individual being treated.

In addition to other factors discussed herein, the amount administered to an individual being treated may depend upon a number of factors, including the species being treated, the weight of the individual being treated, and the individual's condition otherwise. The method specifically involves the prevention and amelioration of motion sickness in human beings, including adult human beings.

As used herein, the terms "patient," "subject," and "individual" may be used interchangeably to refer to a mammal who is administrated tradipitant. Guinea pigs, dogs, cats, gerbils, horses, cattle, sheep, and humans are within the scope of the terms "patient," "subject," and "individual." The most preferred subject is a human being. The term "effective amount," i.e., dose, of tradipitant refers to an amount that is effective in treating or preventing the disorders described herein, or symptoms thereof.

As discussed herein, a first aspect of the disclosure provides an improvement in a method of treating an individual about to engage in an activity involving sickness-inducing motion. According to this aspect, the individual may be a human individual, and the improvement may comprise selecting the individual for treatment based on the ethnicity of the individual. In particular, the improved method may include selecting the individual for treatment based on a Hispanic ethnicity of the individual. Hispanic individuals or subjects may also be referred to as Latinx. Individuals not of Hispanic ethnicity may be, e.g., white (non-Hispanic), Black or African American (non-Hispanic), American Indian and Alaska Native (non-Hispanic), Asian (non-Hispanic), Native Hawaiian and other Pacific Islander (non-Hispanic), some other race (non-Hispanic), or multi-racial (non-Hispanic). (Eric Jensen et al., Measuring Racial and Ethnic Diversity for the 2020 Census, available at https://www.census.gov/newsroom/blogs/random-samplings/2021/08/measuring-racial-ethnic-diversity-2020-census.html (Aug. 4, 2021; last visited Feb. 10, 2023)). The improvement may further include administering tradipitant to the selected individual, i.e. a Hispanic individual, prior to the commencement of the activity, in an amount effective to prevent motion sickness or at least one symptom of motion sickness in the individual.

The activity involving sickness-inducing motion may include vehicle travel, e.g., via automobile, airplane, helicopter, boat, train, or bus. The activity involving sickness-inducing motion may also include any other form of ground or rail transportation, boats under power or sail, ferries, cruise ships, personal watercraft, canoes, kayaks, row boats, amusement rides, certain gymnastic maneuvers such as somersaults, or the use of virtual reality devices or simulators. In certain embodiments in which the sickness-inducing motion includes vehicle travel, the administration of tradipitant may occur about 30 minutes prior to entering the vehicle, and/or about 30 minutes prior to commencement of vehicle travel. For travel by car, for example, these timeframes may be approximately the same, while in the case of travel by airplane or train, the individual may board or enter the vehicle, i.e. airplane or boat, well in advance of commencement of the sickness-inducing motion. The skilled person will be able to adapt the improved methods described herein in accordance with such variables.

In certain embodiments, the symptom of motion sickness to be treated, prevented, or ameliorated may be one or more of nausea, vomiting, dizziness, headache, fullness, or disorientation. In particular, the symptom may be vomiting.

The effective amount of tradipitant administered to an individual in accordance with the foregoing improved method may be, e.g., about 100 to about 400 mg, about 100 to about 300 mg, about 100 to about 200 mg, about 150 to about 400 mg, about 150 to about 300 mg, about 150 to about 200 mg, about 170 mg, or 170 mg. The effective amount of tradipitant may be orally administered in a solid immediate release form comprising tradipitant and one or more pharmaceutically acceptable excipients, and the solid immediate release form may be, e.g., a capsule or a tablet. In certain embodiments, the effective amount may be administered as two 85 mg unit dosage forms, e.g., capsule or tablet, for a total of 170 mg.

According to a second aspect of the disclosure, an improvement is provided for a method of treating an individual suffering from, or expected to suffer from motion sickness or at least one symptom of motion sickness. The at least one symptom of motion sickness is nausea, vomiting, dizziness, headache, fullness, or disorientation. In particular, the symptom may be vomiting.

According to the improvement, the method comprises administering tradipitant to the individual at a dose effective to treat the motion sickness or a symptom thereof, where the effective dose is determined based at least in part on the ethnicity of the individual. In particular, the dose may be a first dose if the individual is Hispanic, and may be a second dose if the individual is non-Hispanic, e.g., if the individual is white (non-Hispanic), Black or African American (non-Hispanic), American Indian and Alaska Native (non-Hispanic), Asian (non-Hispanic), Native Hawaiian and other Pacific Islander (non-Hispanic), some other race (non-Hispanic), or multi-racial (non-Hispanic).

According to this aspect, the second dose may be larger than the first dose, such that Hispanic individuals receive a smaller dose than non-Hispanic individuals.

This may be due to an enhanced treatment effect seen in Hispanic individuals.

In certain embodiments, the administration further comprises oral administration of tradipitant, which may be in a solid immediate release form, e.g., a tablet or a capsule, comprising tradipitant and one or more pharmaceutically acceptable excipients.

In certain embodiments, the first dose may be selected from: about 100 to about 400 mg, about 100 to about 300 mg, about 100 to about 200 mg, about 150 to about 400 mg, about 150 to about 300 mg, about 150 to about 200 mg, about 170 mg, or 170 mg. The first dose may be administered as two unit dosage forms containing, e.g., about 85 mg per unit dosage form. The second dose may be larger, e.g., the second dose may be about 150% of the first dose, or the second dose may be larger than the first dose but may be independently selected from the first dose. In certain embodiments, the second dose may be selected from: about 150 mg to about 600 mg, about 150 mg to about 450 mg, about 150 to about 300 mg, 225 mg to about 600 mg, about 225 mg to about 450 mg, about 225 mg to about 300 mg, about 255 mg, or 255 mg. The second dose may be administered as three unit dosage forms containing, e.g., about 85 mg per unit dosage form, for a total of 255 mg.

In other embodiments, the first dose may be about 85 mg, or may be 85 mg. The first dose may be administered as one unit dosage forms containing, e.g., about 85 mg per unit dosage form. The second dose may be larger, e.g., the second dose may be about 200% of the first dose, or the second dose may be larger than the first dose but selected independently thereof. The second dose may be, e.g., about 100 to about 400 mg, about 100 to about 300 mg, about 100 to about 200 mg, about 150 to about 400 mg, about 150 to about 300 mg, about 150 to about 200 mg, about 170 mg, or 170 mg. The second dose may be administered as two unit dosage forms containing, e.g., about 85 mg per unit dosage form, for a total of 170 mg.

According to a third aspect of the disclosure, a method is provided for treating an individual about to engage in an activity involving sickness-inducing motion. According to this aspect, the individual may be human, and the method may comprise determining an effective dose of tradipitant for the individual, wherein the effective dose is a first dose if the individual is Hispanic, and is a second dose if the individual is non-Hispanic, e.g., if the individual is if the individual is white (non-Hispanic), Black or African American (non-Hispanic), American Indian and Alaska Native (non-Hispanic), Asian (non-Hispanic), Native Hawaiian and other Pacific Islander (non-Hispanic), some other race (non-Hispanic), or multi-racial (non-Hispanic). The method further comprises administering the effective dose of tradipitant to the individual, prior to the commencement of the activity. Regardless of whether the first or second dose is administered to the individual according to this aspect of the disclosure, the effective dose is the dose that is effective to prevent motion sickness or at least one symptom of motion sickness in that particular individual. The symptom may be one or more of nausea, vomiting, dizziness, headache, fullness, or disorientation. In particular, the symptom may be vomiting.

In certain embodiments, the administering further comprises orally administering the tradipitant, which may be in a solid immediate release form comprising tradipitant and one or more pharmaceutically acceptable excipients. The solid immediate form may be, e.g., a capsule or a tablet. In certain embodiments, the second dose may be larger than the first dose, such that non-Hispanic individuals may be administered a larger effective dose than Hispanic individuals.

In certain embodiments, the first dose may be selected from: about 100 to about 400 mg, about 100 to about 300 mg, about 100 to about 200 mg, about 150 to about 400 mg, about 150 to about 300 mg, about 150 to about 200 mg, about 170 mg, or 170 mg. The first dose may be administered as two unit dosage forms containing, e.g., about 85 mg per unit dosage form, for a total of 170 mg. The second dose may be larger, e.g., the second dose may be about 150% of the first dose, or the second dose may be larger than the first dose but may be independently selected from the first dose. In certain embodiments, the second dose may be selected from: about 150 mg to about 600 mg, about 150 mg to about 450 mg, about 150 to about 300 mg, 225 mg to about 600 mg, about 225 mg to about 450 mg, about 225 mg to about 300 mg, about 255 mg, or 255 mg. The second dose may be administered as three unit dosage forms containing, e.g., about 85 mg per unit dosage form, for a total of 255 mg.

In other embodiments, the first dose may be about 85 mg, or may be 85 mg. The first dose may be administered as one unit dosage forms containing, e.g., about 85 mg per unit dosage form. The second dose may be larger, e.g., the second dose may be about 200% of the first dose, or the second dose may be larger than the first dose but selected independently thereof. The second dose may be, e.g., about 100 to about 400 mg, about 100 to about 300 mg, about 100 to about 200 mg, about 150 to about 400 mg, about 150 to about 300 mg, about 150 to about 200 mg, about 170 mg, or 170 mg. The second dose may be administered as two unit dosage forms containing, e.g., about 85 mg per unit dosage form, for a total of about 170 mg.

The skilled artisan will appreciate that additional preferred embodiments may be selected by combining the preferred embodiments above, or by reference to the examples given herein.

EXAMPLES

Example 1: Pre-Clinical Studies

Tradipitant is a selective neurokinin-1 (NK-1) receptor antagonist. In vitro, tradipitant potently inhibits NK-1 receptor binding and antagonizes the effects of an NK-1 agonist in a functional assay. No significant activity is observed in a panel of 74 additional receptors, enzymes, and ion channels including the NK-2 and NK-3 receptors. By 3 different measures, tradipitant is also a potent centrally active NK-1 antagonist in vivo.

Example 1.1: Mechanism Studies

Tradipitant inhibits [$^{125}$I]substance P (SP) binding to the NK-1 receptor expressed by IM-9 cells with a $K_i$ of 0.062 nM and inhibits the SP-induced mobilization of intracellular calcium in U373 cells with a $K_b$ of 0.095 nM (Table 1).

TABLE 1

Affinity of tradipitant for NK-1 Receptors In Vitro

| Antagonist | IM-9 Human Cell Membrane Binding $K_i$ (nM) | Calcium Mobilization in U373 Cells $K_b$ (nM) |
|---|---|---|
| Tradipitant | 0.062 ± 0.012 | 0.095 ± 0.025 |
| Aprepitant | 0.14 ± 0.03 | 0.14 ± 0.01 |
| CP-122721 | 0.027 ± 0.01 | 0.034 ± 0.009 |

These potencies are similar to those observed with the NK-1 antagonists aprepitant (MK-869) and CP-122721. In addition, results from tradipitant evaluation in a panel of 74 other receptors, enzymes, and ion channels indicate that, at a test concentration of 1 μM, tradipitant does not exhibit any inhibition of binding greater than 50%. At the NK-2 and NK-3 receptors, the compound produces no significant inhibition. Therefore, tradipitant is a highly selective NK-1 antagonist in vitro.

As shown in Table 2, several of the major metabolites of tradipitant have an affinity for the NK-1 receptor based on a binding assay. These metabolites have high affinity for the NK-1 receptor.

TABLE 2

Affinity of tradipitant metabolites for NK-1 Receptors in vitro

| Metabolite | Designation | IM-9 Human Cell Membrane Binding $K_i$ (nM) |
|---|---|---|
| LSN2081070 | M2 (Racemic) | 0.09 (n = 1) |
| LSN2107355 | M2 (S-enantiomer) | 0.08 (n = 1) |
| LSN2107357 | M2 (R-enantiomer) | 0.94 (n = 1) |
| LSN2195411 | M3 | 0.03 (n = 1) |
| LSN2195413 | M4 (Racemic) | 0.08 (n = 1) |

Example 1.2: Efficacy Models for In Vivo Evaluation of Brain NK-1 Receptor Occupancy and Efficacy of Tradipitant

Example 1.2.1: Effects of Tradipitant on Centrally Administered NK-1 Agonist-Induced Foot-Tapping Behavior in Gerbils

Introduction

Differences in species selectivity of NK-1 receptors pose challenges to characterization of NK-1 receptor antagonists in vivo. Gerbil NK-1 receptors have previously been shown to be similar to those in humans. Gerbils exhibit a characteristic stereotypic foot-tapping behavior in response to distress, fear, or aversive stimuli. Intracerebroventricular (icy) administration of substance P or a selective NK-1 receptor agonist such as GR73632 produces rapid rhythmic tapping of the hind feet lasting approximately 5 minutes, which can be inhibited by systemic administration of a brain penetrating antagonist of the NK-1 receptor. This response is selective for NK-1 agonists, since selective NK-2 and NK-3 agonists do not elicit a similar response. This behavioral response is further characterized and modified to enable identification and optimization, in vivo, of potent NK-1 receptor antagonists including tradipitant.

Methods

Male Mongolian gerbils (Harlan Sprague Dawley, Indianapolis, IN) weighing 26 to 40 grams are administered the selective neurokinin-1 receptor agonist GR73632 (3 pmol) via direct, vertical, free-hand intracerebroventricular (icy) injection to a depth of 4.5 mm below bregma with a cuffed 27-gauge needle attached to a 50 μl Hamilton syringe. Immediately after injection, animals are placed individually into isolated chambers with pressure-sensitive velocimeter platform floors (San Diego Instruments acoustic startle apparatus) that detect and quantify vibration. The San Diego Instruments "SR" DOS-based computer program is used on a PC to record the number of foot-taps over the following 6 to 10 minutes, beginning 30 seconds after the floor is lightly tapped. Raw data are converted with a Microsoft® Excel® (Microsoft® and Excel® are registered trademarks of Microsoft Corp., Redmond, WA) macro that determines the number of events over threshold (125) in each 250-millisecond time bin over the 5.5 minutes following onset of observation. The total number and average intensity of events over the duration is determined. Total number of taps is analyzed with one-way ANOVA and post-hoc Dunnett's test using JMP statistical software.

A dose-response curve (with doses of 0.3, 1, 3 and 10 pmols, icy) is initially generated with the NK-1 agonist GR73632. Maximal foot-tapping behavior is achieved with 3 and 10 pmol doses; the 3 pmol dose is subsequently chosen as the dose of choice for antagonism experiments.

NK-1 antagonists are tested for their ability to attenuate GR73632-induced foot tapping. NK-1 antagonists are administered (po) via oral feeding tube at doses and time points specified in each experiment. All animals receive only one dose of NK-1 antagonists in all tests.

$ED_{50}$ Determinations/Dose-Response Tests

NK-1 antagonists are administered at multiple doses (at least 3; one dose per animal) and response to GR73632 is measured.

Duration of Action Tests

NK-1 receptor antagonists are administered at multiple pre-treatment times (one administration per animal) including at 0.5, 1, 2, 4, 7, 16, and 24 hours prior to GR73632 injection. GR73632 (Peninsula Labs, CA) is dissolved in saline. Tradipitant is dissolved in 1% CMC/0.5% SLS/0.085% PVP vehicle. CP-122721 and aprepitant are synthesized at Lilly Laboratories and dissolved in 10% ethanol/emulphor and 1% CMC/0.5% SLS/0.085% PVP respectively.

Results

As shown in FIG. 1, orally administered tradipitant potently inhibits NK-1 agonist-induced foot-tapping behavior in gerbils 2 hours after administration of drug in a dose-dependent manner, with an $ED_{50}$ of 0.03±0.004 mg/kg (*$p<0.05$ compared to vehicle for 0.1 mg/kg and 0.3 mg/kg doses). Data shown in FIG. 1 are expressed in number of foot-tapping events occurring in five (5) minutes.

Figure 2:
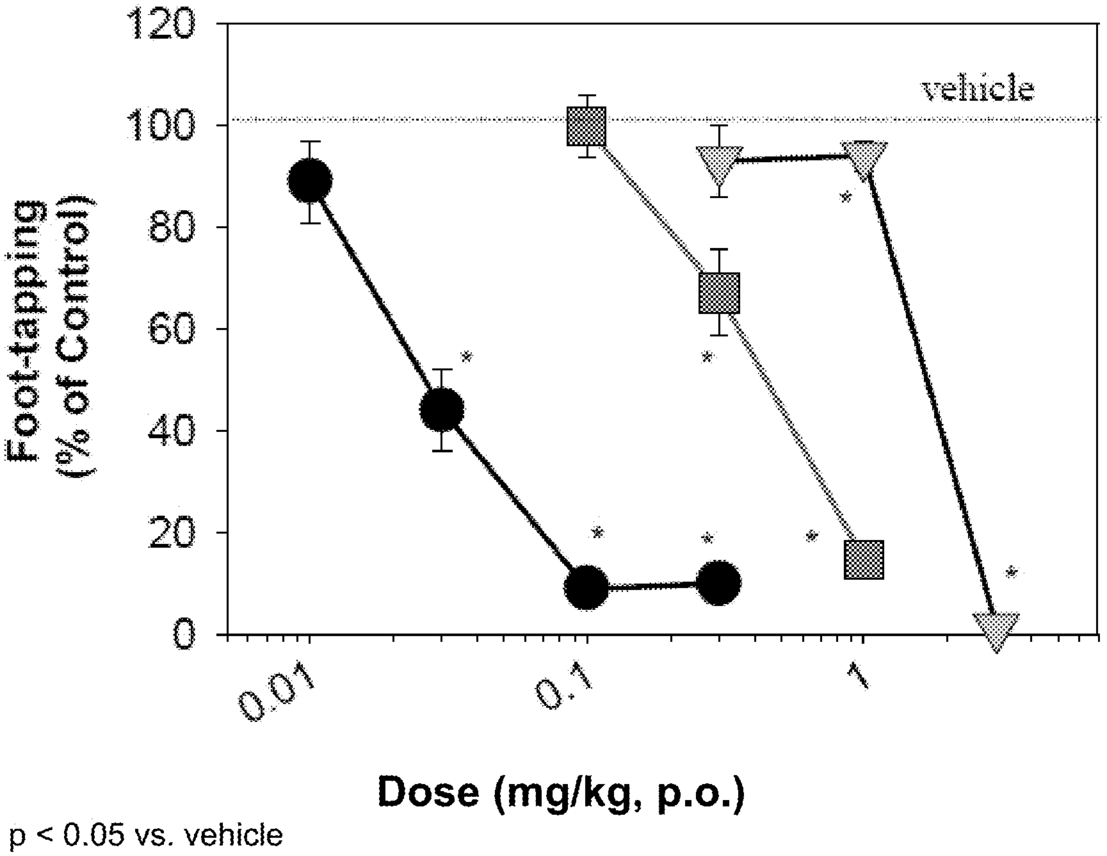
FIG. 2 illustrates the effect of tradipitant on NK-1 agonist (GR73632, 3 pmol, icv)-induced foot-tapping behavior after oral administration: comparison with other NK-1 antagonists, aprepitant and CP-122721: dose response.

FIG. 2 depicts a comparison of the efficacy of tradipitant to that of other NK-1 antagonists, with data expressed as percent control of vehicle (vehicle response to 3 pmol GR73632). Tradipitant is found to be more potent than aprepitant (Merck, $ED_{50}$=0.42 mg/kg±0.05 mg/kg) and CP-122721 (Pfizer, $ED_{50}$=2.2 mg/kg±0.5 mg/kg).

Figure 3:
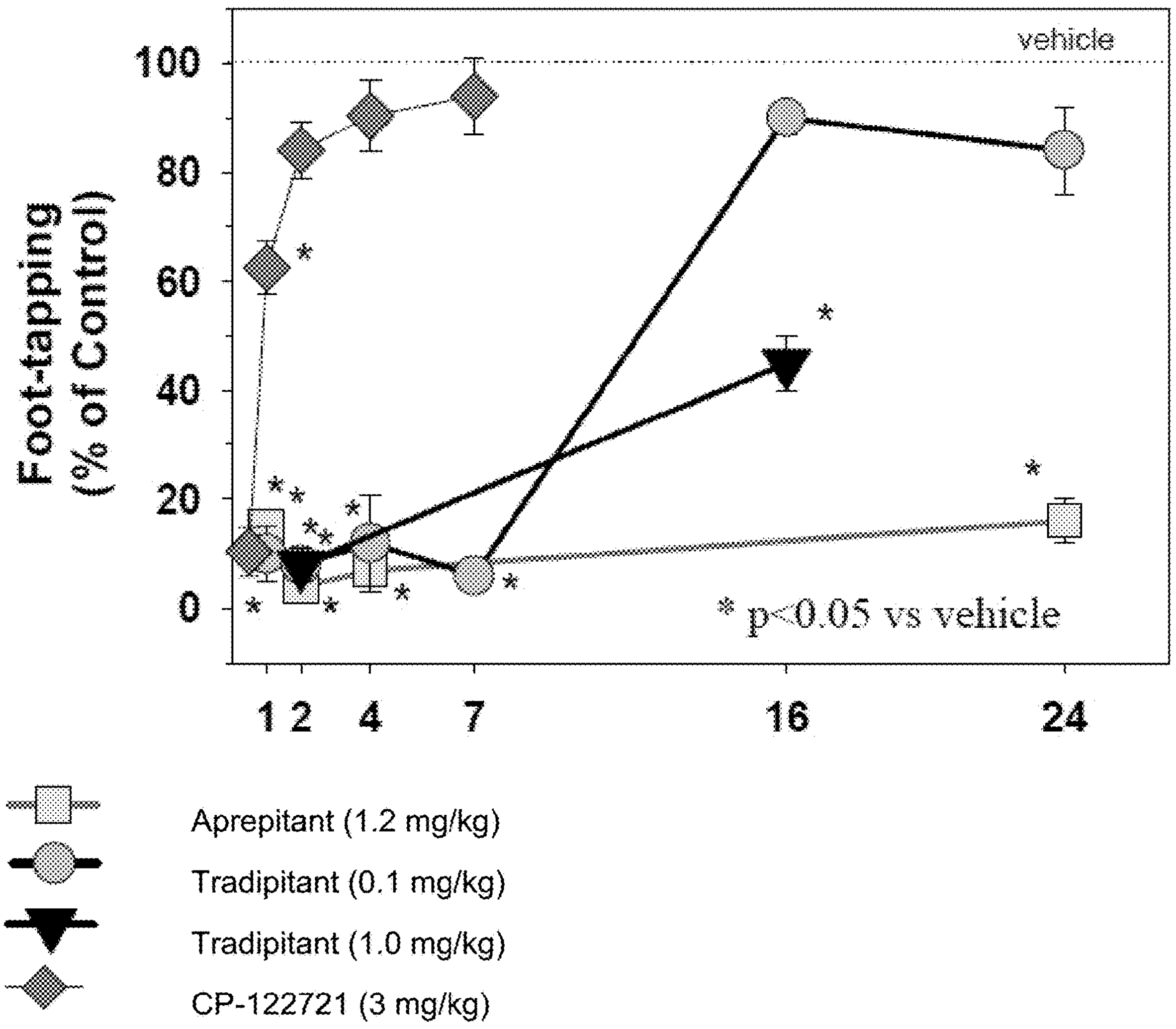
FIG. 3 illustrates the effect of tradipitant on NK-1 agonist (GR73632, 3 pmol, icv)-induced foot-tapping behavior after oral administration: comparison with other NK-1 antagonists, aprepitant and CP-122721: time course.

FIG. 3 depicts the effects of tradipitant over a time course on NK-1 agonist (GR 73632, 3 pmol, icv)-induced foot-tapping behavior after oral administration, compared with that of NK-1 antagonists aprepitant and CP-122721. Tradipitant (0.1 mg/kg, po) is found to significantly inhibit foot-tapping behavior up to 7 hours after administration but the effect is significantly diminished by 16 hours after administration at this dose. However, at a higher dose of 1 mg/kg, tradipitant shows greater than 50% inhibition of foot-tapping behavior 16 hours after administration. The duration of effect of tradipitant is longer than that of CP-122721 (up to 2 hours after administration, 3 mg/kg) while aprepitant (1 mg/kg) shows inhibition of foot-tapping behavior up to 24 hours after administration. Data are expressed as percent control of vehicle (vehicle response to 3 pmol GR73632).

Discussion

The effect of tradipitant on NK-1 agonist-induced foot-tapping behavior in gerbils suggests that tradipitant is a very potent, centrally acting NK-1 receptor antagonist in vivo in the gerbil with a relatively long duration of action.

Example 1.2.2: Emetic Challenge Study in Beagle Dogs with Tradipitant

Introduction

Five male dogs are administered a single oral dose of 3 mg/kg aprepitant (a positive control), or tradipitant at 0.3, 1.0, and 3.0 mg/kg in a Latin-square design. An intravenous injection of 0.1 mg/kg apomorphine, a known emetic, is given alone, or 2 hours after administration of tradipitant or aprepitant. Each animal is administered a different dose on a particular dosing day, so that each dose of tradipitant, aprepitant, and apomorphine alone is represented. Over the five (5) weeks of the study, each animal receives each of the treatments, but only one per week. The purpose of this study is to determine if tradipitant suppresses apomorphine-induced emesis.

The low dose of tradipitant is 10 times the $ED_{50}$ in the gerbil foot-tapping model of NK-1 receptor antagonism (Example 1.2.1). The high dose is 100 times this efficacious dose, and is also the dose of aprepitant that has previously been determined to be efficacious against apomorphine-induced emesis in the dog. The mid dose of tradipitant is the approximate half-log interval between the low and high doses.

The oral route of administration is selected for tradipitant because this is the route proposed or currently used clinically. The intravenous route is typically used for experimental apomorphine administration. The beagle dog is considered an effective species for demonstration of antagonism of apomorphine-induced emesis.

Methods

A single oral dose of 0, 0.3, 1.0, or 3.0 mg/kg tradipitant, or 3.0 mg/kg aprepitant is administered to each male dog once a week in gelatin capsules. All animals are dosed over a period of five (5) weeks, with each dog receiving one of five different treatments on each day of dosing. A dose of 0.1 mg/kg apomorphine is administered by intravenous injection approximately two (2) hours after each administration of tradipitant or aprepitant. In cases where apomorphine is administered alone, without prior treatment with tradipitant or aprepitant, apomorphine is given at approximately the same time as when given in combination with tradipitant or aprepitant.

All dogs are fasted overnight prior to each treatment day and then fed approximately one (1) hour after oral dosing (approximately one (1) hour prior to administration of apomorphine). Individual doses are adjusted weekly for changes in body weight.

The dose regimen consists of a 5×5 Latin square design, in which each subject receives 1 dose or dose combination per week (6 day washout) as shown in Table 3 below.

TABLE 3

Latin Square Design

| | Study week | | | | |
|---|---|---|---|---|---|
| | 1 | 2 | 3 | 4 | 5 |
| Dog 1 | APO + 0.3 mg/kg tradipitant | APO + aprepitant | APO + 3 mg/kg tradipitant | APO | APO + 1 mg/kg tradipitant |
| Dog 2 | APO + aprepitant | APO + 1 mg/kg tradipitant | APO | APO + 0.3 mg/kg tradipitant | APO + 3 mg/kg tradipitant |
| Dog 3 | APO + 3 mg/kg tradipitant | APO | APO + aprepitant | APO + 1 mg/kg tradipitant | APO + 0.3 mg/kg tradipitant |

TABLE 3-continued

Latin Square Design

| | Study week | | | | |
|---|---|---|---|---|---|
| | 1 | 2 | 3 | 4 | 5 |
| Dog 4 | APO | APO + 0.3 mg/kg tradipitant | APO + 1 mg/kg tradipitant | APO + 3 mg/kg tradipitant | APO + aprepitant |
| Dog 5 | APO + 1 mg/kg tradipitant | APO + 3 mg/kg tradipitant | APO + 0.3 mg/kg tradipitant | APO + aprepitant | APO |

The number of emetic episodes is recorded for approximately one hour following the injection of apomorphine, and plasma concentrations at anticipated Tmax of tradipitant (2 hours post-dosing) are evaluated.

Results

Table 4 provides individual and mean and standard deviation values for the 2 hour plasma concentrations of tradipitant. All animals administered tradipitant have measurable levels at 2 hours post-dose. In general, plasma concentrations at 2 hours post-dose increase with increasing dose in a sub-proportional manner. As observed in other studies in dogs, the exposure to tradipitant is variable between animals. Individual animal data reveal no relationship between plasma concentrations and week of administration.

TABLE 4

Plasma concentrations of tradipitant (ng/ml)

| | Administered Dose | | |
|---|---|---|---|
| | 0.3 mg/kg Concentration of tradipitant (ng/ml) | 1.0 mg/kg Concentration of tradipitant (ng/ml) | 3.0 mg/kg Concentration of tradipitant (ng/ml) |
| Dog 1 | 51.20 | 175.58 | 122.73 |
| Dog 2 | 41.33 | 86.49 | 256.58 |
| Dog 3 | 90.93 | 240.84 | 316.20 |
| Dog 4 | 83.38 | 100.97 | 682.91 |
| Dog 5 | 22.59 | 61.56 | 119.79 |
| Mean (SD) | 57.89 (28.75) | 133.09 (73.71) | 299.64 (230.58) |

As shown in Table 5, emesis occurs after each treatment, with the largest incidence of emesis occurring in the apomorphine alone group. One dog (Dog 3) has a single episode of emesis at each dose of tradipitant and aprepitant; this dog also has the greatest number of emetic episodes with apomorphine alone (12). No emesis occurs in the remaining four (4) dogs at any dose of tradipitant or aprepitant. These dogs have an average of four (4) emetic episodes with apomorphine alone. The antiemetic effect of aprepitant supports the validity of this model.

TABLE 5

Emetic episodes by treatment group

| Test article* | Dose level (mg/kg) | Total No. Emetic Episodes |
|---|---|---|
| APO (control) | 0 | 28 |
| aprepitant | 3.0 | 1** |
| tradipitant | 0.3 | 1** |
| tradipitant | 1.0 | 1** |
| tradipitant | 3.0 | 1** |

*Apomorphine is administered as a challenge dose to all groups.

**All episodes occur in same dog (Dog 3).

Results of this study indicate that tradipitant is effective against apomorphine-induced emesis at each dose tested (0.3, 1.0, and 3.0 mg/kg).

Example 1.2.3: Tradipitant Inhibits Substance P-Induced Vocalization in Guinea Pigs Introduction When introduced into the brain, the NK-1 receptor agonist substance P (SP) elicits distress vocalizations in the guinea pig that can be inhibited by NK-1 antagonists. This behavioral assay is used to demonstrate potency and CNS penetration of NK-1 antagonists in the guinea pig, a species that has receptor affinity for NK-1 antagonists that is similar to humans.

Methods

Figure 5:
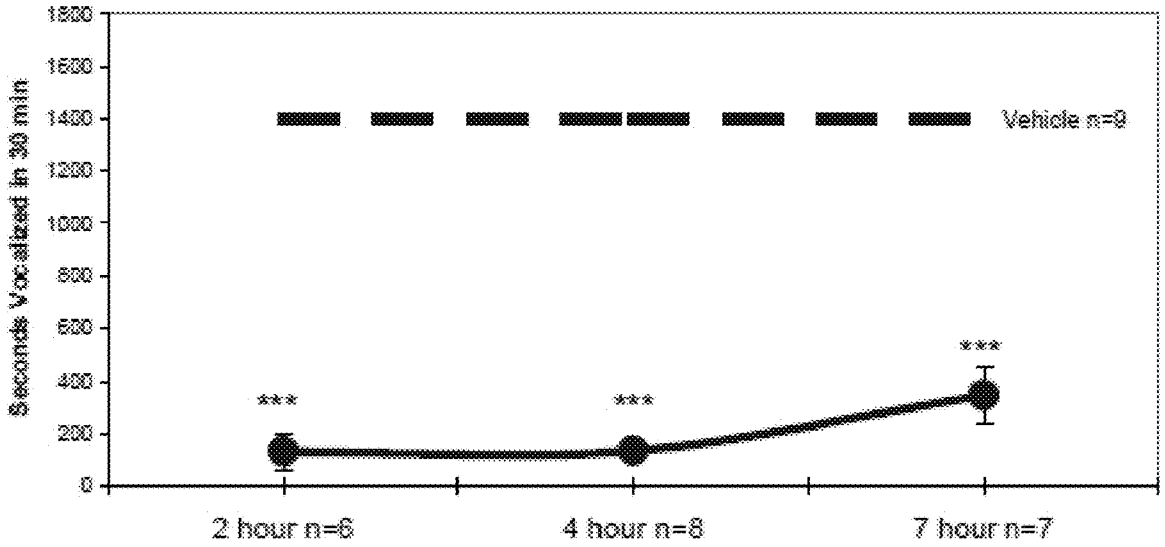
FIG. 5 illustrates the duration of activity, i.e. suppression of NK-1 agonist-induced vocalization in guinea pigs, following a 0.1 mg/kg dose of tradipitant.
Figure 6:
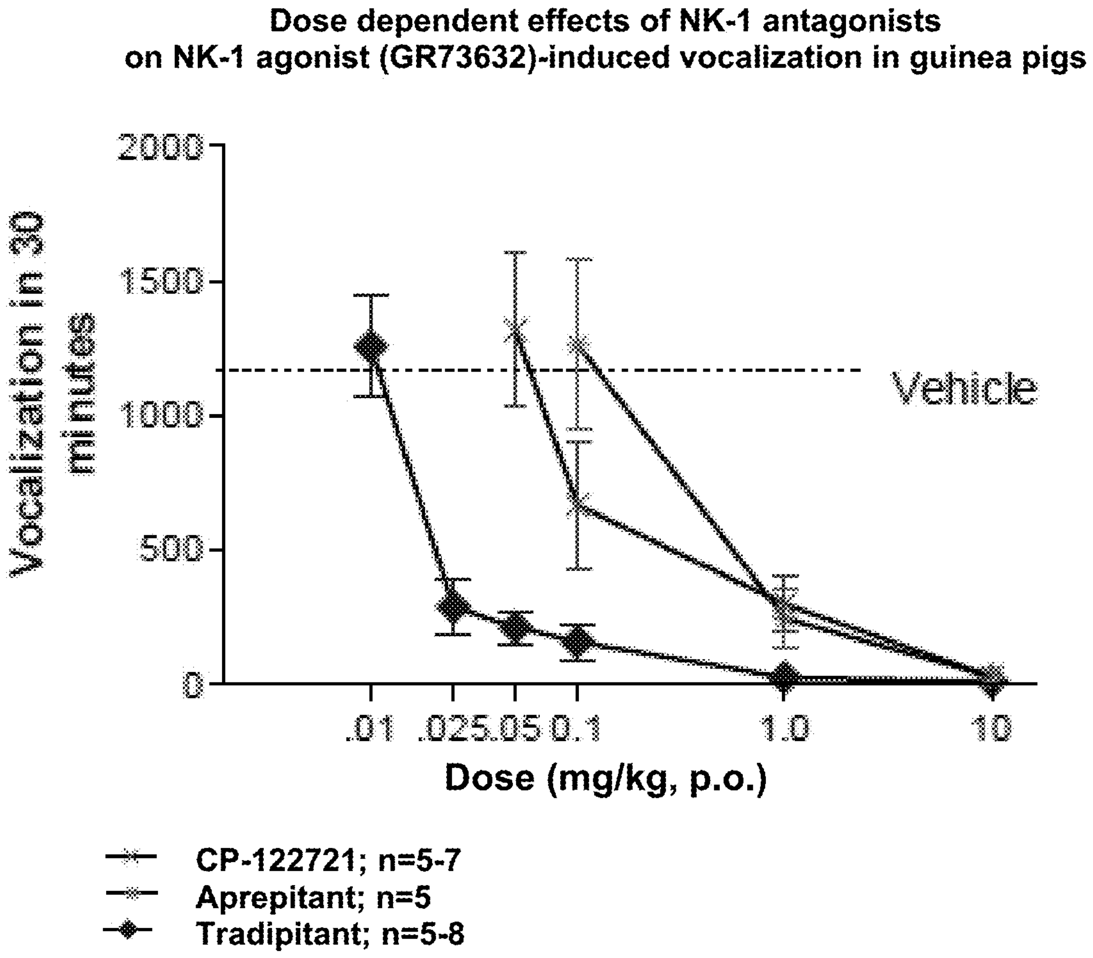
FIG. 6 illustrates the dose-dependent effects of tradipitant, and the effects of various NK-1 antagonists in the guinea pig vocalization assay.

Male Dunkin/Hartley guinea pigs (200 to 250 grams) are orally administered either vehicle or an NK-1 antagonist. Approximately 45 minutes later (for dose response studies), the animals are anesthetized and 0.1 nmol of GR73632 (SP analog) in a vehicle volume of 5 μl is injected into the cerebral ventricle at the intersection of bregma and the midline of the skull. Animals are placed in a dark testing chamber located inside of a sound attenuation cubicle and vocalizations are recorded for 30 minutes following recovery from anesthesia. The time spent vocalizing is quantified for each animal. In the duration of action study, 0.1 mg/kg of tradipitant or vehicle solution is administered orally and then 2, 4, or 7 hours later, 0.1 nmol of GR73632 is administered into the cerebral ventricle as described above. Vocalizations are recorded and quantified as indicated above. Vehicle solutions are either CMC (FIG. 4 data) or an ethanol/emulphor solution (FIGS. 5 and 6). Data is analyzed using one-tailed t-tests.

Results

Figure 4:
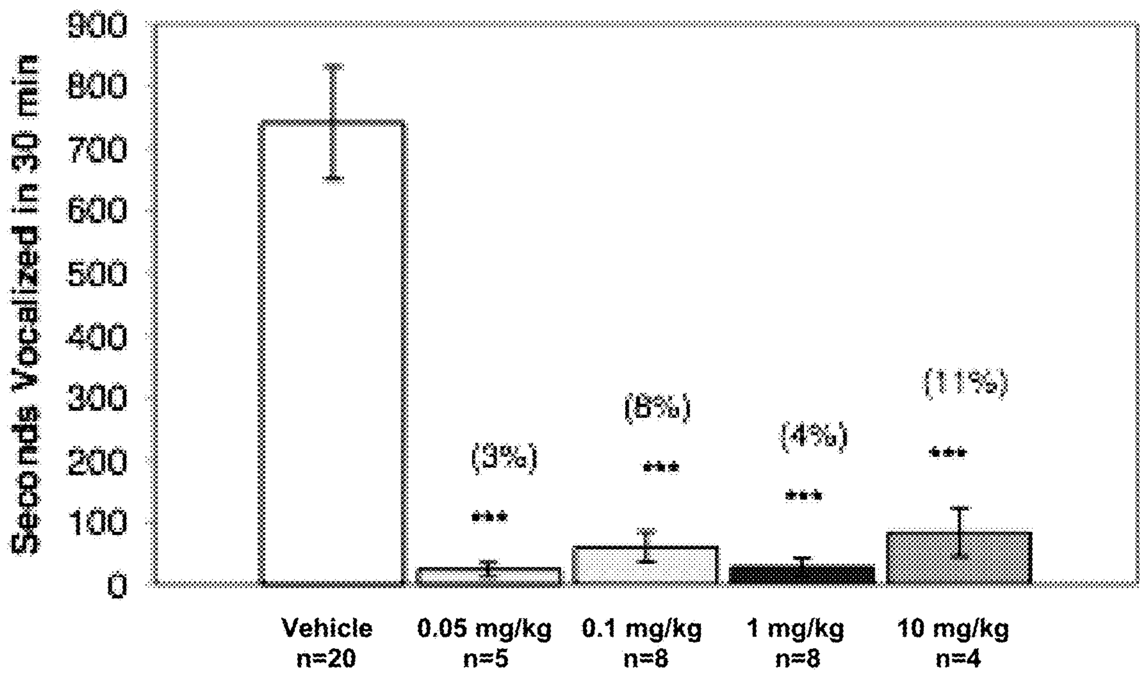
FIG. 4 illustrates the effect of tradipitant on GR73632-induced vocalization in guinea pigs across a concentration range of 0.05 to 10 mg/kg.

As shown in FIG. 4, oral administration of tradipitant produces significant inhibition of agonist-induced vocalization at doses of 10 mg/kg ($p<0.001$), 1.0 mg/kg ($p<0.001$), 0.1 mg/kg ($p<0.001$), and 0.05 mg/kg ($p<0.001$). Data shown parenthetically in FIG. 4 indicate percent of control response. Activity of tradipitant does not wane at the lower doses, indicating that even lower doses would be required to produce a dose response function.

As shown in FIG. 5, the effect of 0.1 mg/kg tradipitant is significantly active in suppressing agonist-induced vocalization at 7 hours following oral administration of the antagonist compound.

A second dose-response study compares potencies of tradipitant, aprepitant, and CP-122721. As shown in FIG. 6, all NK-1 antagonists tested produce significant inhibition of vocalization at 1 mg/kg. Only tradipitant retains significant inhibitory activity at and below 0.1 mg/kg. The minimum effective dose of tradipitant is found to be 0.025 mg/kg which produces highly significant ($p<0.001$) inhibition of vocalization compared to controls. (Vehicle was ethanol/emulphor; vehicle groups were n=5-14 per compound.)

Discussion

Tradipitant significantly inhibits NK-1 agonist-induced vocalization in guinea pigs, indicating that this compound is an orally available and brain-penetrant NK-1 antagonist. The minimum effective dose (MED) that produces this effect is 0.025 mg/kg. Tradipitant, administered orally, is shown to have a duration of activity that exceeds 7 hours. In this experimental paradigm, tradipitant is substantially more potent than aprepitant and CP-122721.

Example 1.2.4: Occupancy of NK-1 Receptors

A tracer NK-1 antagonist compound (GR205171) is used to evaluate the ability of other NK-1 antagonists to occupy the brain NK-1 receptors. In these studies, the test compounds are administered orally and the tracer compound is administered intravenously afterward. The occupancy of the NK-1 receptors is evaluated by quantitating the amount of the tracer compound bound to the brain NK-1 receptors after increasing doses of the test compounds. Using this paradigm, tradipitant has an estimated $ED_{50}$ of 0.04 mg/kg p.o. and is substantially more potent than the other antagonists evaluated.

Example 2: Clinical Study of Gastrointestinal Motility

A single-center, randomized, double-blind, placebo-controlled study is conducted to investigate the effect of tradipitant on small bowel transit time. A total of 15 healthy subjects, including 12 men and 3 women between the ages of 19 and 63 years, are enrolled in the study and receive at least 1 dose of study medication. A total of 13 subjects complete the study. Subjects are randomized to receive 20 mg of tradipitant, 200 mg of tradipitant, or placebo as a single oral dose within each of 3 periods, co-administered with a capsule radiolabeled with a maximum of 1MBq $^{111}$In. Four hours post-dose, all subjects also receive a second capsule radiolabeled with a maximum of 4MBq $^{99m}$Tc. Each subject receives all 3 doses during the study. For all dosing regimens, in vivo gamma scintigraphic studies are performed at predetermined intervals, and the following scintigraphic parameters are analyzed: onset and completion of gastric emptying, onset and completion of colon arrival, initiation and completion of small bowel transit, and initial and complete disintegration of the capsule (anatomical location and time).

A statistically significant effect of tradipitant on small bowel transit time is observed in the study. No effect on gastric emptying is observed in this study. However, the study is underpowered with respect to this parameter.

Example 3: Motion Sickness Prevention

A randomized, double blind, placebo-controlled clinical study of motion sickness is conducted, in which 126 human subjects ("study participants"), each having a prior history of motion sickness, are subjected to sea travel in the Pacific Ocean under varied weather conditions.

Methods

Study participants are distributed over seven (7) four-hour boat trips off the coast of Los Angeles, California, USA. For each trip, sea conditions and participant self-evaluation of symptoms of motion sickness are recorded. Among the seven trips, three are under "rough" sea conditions, conducive to producing motion sickness with wave heights above one meter. The remaining four trips are made under "calm" conditions, with wave heights less than one meter, and are less likely to produce motion sickness. Under "rough" sea conditions, 72.2% of the placebo treated patients experience vomiting compared to only 26.7% under "calm" conditions.

Subjects are randomized 1:1 to receive either tradipitant 170 mg or placebo by mouth in a blinded fashion, prior to travel initiation. Participants report their symptoms at predetermined time intervals of every 30 minutes during the travel period using the Motion Sickness Severity Scale (MSSS) and other assessments. Primary end points of the study include: percentage of participants vomiting, and Motion Sickness Severity Scale (MSSS) Worst score. The MSSS is a 7 point scale ranging from 0 ("no symptoms") to 6 ("vomiting"). An exploratory analysis is also performed to evaluate the effects of tradipitant under "calm" and "rough" seas.

Results

Results are reported in Table 6 below. In the overall intent to treat (ITT) population (n=126) and across all boat trips, a significantly higher percentage of participants experience vomiting in the placebo arm of the study (39.7%) as compared to the tradipitant arm (17.5%), p value=0.0039. The MSSS Worst score endpoint also favors tradipitant (3.4) vs. placebo (3.75), although the difference does not reach statistical significance, p value=0.293. Under "calm" sea conditions, only a small percentage of participants in either arm experience vomiting, 26.7% in the placebo arm and 18.2% in the tradipitant treatment arm (not significant). A similar MSSS Worst score is seen between the two groups under "calm" conditions, 3.32 (placebo arm) and 3.40 (tradipitant treatment arm) (not statistically significant). Under "rough" sea conditions, 72.2% of the placebo treated patients vomit as compared to 15.8% of those treated with tradipitant, p value=0.0009. A significant effect is also seen under "rough" conditions in the MSSS Worst score, 4.57 (placebo) and 3.19 (tradipitant), p value=0.0235.

TABLE 6

Results for the Overall population and for the Calm and Rough Sea sub-populations.

| | | Tradipitant | Placebo | Difference | P-value |
|---|---|---|---|---|---|
| | ITT* | n = 63 | n = 63 | | |
| % Vomiting | | 17.5% | 39.7% | 22.2% | 0.0039 |
| Worst MSSS | | 3.40 | 3.75 | 0.35 | 0.2936 |
| | Calm Sea | n = 44 | n = 45 | | |
| % Vomiting | | 18.2% | 26.7% | 8.5% | 0.3123 |
| Worst MSSS | | 3.4 | 3.32 | −0.09 | 0.8271 |
| | Rough Sea | n = 19 | n = 18 | | |
| % Vomiting | | 15.8% | 72.2% | 56.4% | 0.0009 |
| Worst MSSS | | 3.19 | 4.57 | 1.38 | 0.0235 |

Conclusions

The foregoing data show that treatment with 170 mg tradipitant by mouth prior to travel initiation provides a significant reduction in the incidence of vomiting and in MSSS Worst score during travel under rough sea conditions and in overall conditions, as well as modest (not statistically significant) reductions during travel under calm conditions. These findings show that tradipitant at a dose of 170 mg provides an effective treatment for motion sickness.

Example 4

In the study described above in Example 3, further analysis is conducted with respect to study participants' ethnic backgrounds, in particular, whether study participants are Hispanic or non-Hispanic, e.g., white (non-Hispanic), Black or African American (non-Hispanic), American Indian and Alaska Native (non-Hispanic), Asian (non-Hispanic), Native Hawaiian and other Pacific Islander (non-Hispanic), some other race (non-Hispanic), or multi-racial (non-Hispanic). Results are analyzed based on study participants' self-reported ethnic backgrounds.

Results

In the tradipitant treatment arm of the study described in Example 3, Hispanic study participants experience significantly lower incidence of vomiting as compared to non-Hispanic study participants. In particular, 4.5% of Hispanic study participants experience vomiting, while 24.4% of non-Hispanic study participants experience vomiting (p=0.036).

In contrast, in the placebo arm, vomiting incidence does not significantly differ between Hispanic and non-Hispanic study participants: 33.3% of Hispanic study participants experience vomiting, while 42.8% of non-Hispanic study participants experience vomiting (p=0.41).

Conclusions

Administration of tradipitant at a dose of 170 mg for the treatment or prevention of motion sickness and symptoms thereof, results in a lower incidence of vomiting in Hispanic study participants than in non-Hispanic study participants and in the overall tradipitant treatment arm participants. This difference between Hispanic and non-Hispanic subjects is not observed in the placebo arm. This suggests that tradipitant at a dose of 170 mg has a stronger treatment effect in Hispanic individuals than non-Hispanic individuals.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mg, or, more specifically, about 5 mg to about 20 mg," is inclusive of the endpoints and all intermediate values of the ranges of "about 5 mg to about 25 mg," etc.).

Embodiments

Embodiments of the present disclosure may include the following features:

Embodiment 1. An improvement in a method of treating an individual about to engage in an activity involving sickness-inducing motion, the improvement comprising: selecting the individual for treatment based on an ethnicity of the individual, wherein the individual is Hispanic; and administering tradipitant to the individual, prior to the commencement of the activity, in an amount effective to prevent motion sickness or at least one symptom of motion sickness in the individual.

Embodiment 2. The improvement of embodiment 1, wherein the activity is vehicle travel.

Embodiment 3. The improvement of embodiment 2, wherein the administration occurs about 30 minutes prior to entering a vehicle.

Embodiment 4. The improvement of embodiment 2, wherein the administration occurs about 30 minutes prior to commencement of vehicle travel.

Embodiment 5. The improvement of any of embodiments 1-4, wherein the effective amount is 100-400 mg.

Embodiment 6. The improvement of embodiment 5, wherein the effective amount is 100-300 mg.

Embodiment 7. The improvement of embodiment 6, wherein the effective amount is 100-200 mg.

Embodiment 8. The improvement of embodiment 7, wherein the effective amount is about 170 mg.

Embodiment 9. The improvement of embodiment 8, wherein the effective amount is 170 mg.

Embodiment 10. The improvement of any of embodiments 1-9, further comprises orally administering the effective amount of tradipitant.

Embodiment 11. The improvement of embodiment 10, wherein the tradipitant is orally administered in a solid immediate release form comprising tradipitant and one or more pharmaceutically acceptable excipients.

Embodiment 12. The improvement of embodiment 11, wherein the solid immediate release form comprises a capsule or a tablet.

Embodiment 13. The improvement of any of embodiments 2-4, wherein the vehicle travel is via automobile, airplane, helicopter, boat, train, or bus.

Embodiment 14. The improvement of any of embodiments 1-13, wherein the at least one symptom is nausea, vomiting, dizziness, headache, fullness, or disorientation.

Embodiment 15. The improvement of any of embodiments 1-13, wherein the at least one symptom is vomiting.

Embodiment 16. An improvement in a method of treating an individual with motion sickness or at least one symptom of motion sickness, comprising: administering tradipitant to the individual at a dose effective to treat the sickness or a symptom thereof, wherein the dose effective to treat the sickness or the symptom thereof is determined based on an ethnicity of the individual, and wherein the dose is a first dose if the individual is Hispanic, and is a second dose if the individual is non-Hispanic.

Embodiment 17. The improvement of embodiment 16, wherein the second dose is larger than the first dose.

Embodiment 18. The improvement of embodiment 16 or 17, wherein the first dose is 100-400 mg.

Embodiment 19. The improvement of embodiment 18, wherein the first dose is 100-300 mg.

Embodiment 20. The improvement of embodiment 19, wherein the first dose is 100-200 mg.

Embodiment 21. The improvement of embodiment 20, wherein the first dose is about 170 mg.

Embodiment 22. The improvement of embodiment 21, wherein the first dose is 170 mg.

Embodiment 23. The improvement of any one of embodiments 18-22, wherein the second dose is about 150 mg to about 600 mg.

Embodiment 24. The improvement of embodiment 23, wherein the second dose is about 150 mg to about 450 mg.

Embodiment 25. The improvement of embodiment 24, wherein the second dose is about 150 to about 300 mg.

Embodiment 26. The improvement of embodiment 25, wherein the second dose is about 255 mg.

Embodiment 27. The improvement of embodiment 26, wherein the second dose is 255 mg.

Embodiment 28. The improvement of embodiment 16 or 17, wherein the second dose is 100-400 mg.

Embodiment 29. The improvement of embodiment 28, wherein the second dose is 100-300 mg.

Embodiment 30. The improvement of embodiment 29, wherein the second dose is 100-200 mg.

Embodiment 31. The improvement of embodiment 30, wherein the second dose is about 170 mg.

Embodiment 32. The improvement of embodiment 31, wherein the second dose is 170 mg.

Embodiment 33. The improvement of any one of embodiments 28-32, wherein the first dose is about 85 mg.

Embodiment 34. The improvement of embodiment 33, wherein the first dose is 85 mg.

Embodiment 35. The improvement of any one of embodiments 16-34, wherein the administration further comprises oral administration of tradipitant.

Embodiment 36. The improvement of embodiment 35, wherein the tradipitant is orally administered in a solid immediate release form comprising tradipitant and one or more pharmaceutically acceptable excipients.

Embodiment 37. The improvement of embodiment 36, wherein the solid immediate release form further comprises a tablet.

Embodiment 38. The improvement of embodiment 36, wherein the solid immediate release form further comprises a capsule.

Embodiment 39. The improvement of any one of embodiments 16-38, wherein the at least one symptom is nausea, dizziness, headache, fullness, or disorientation.

Embodiment 40. The improvement of any one of embodiments 16-39, wherein the at least one symptom is vomiting.

Embodiment 41. A method of treating an individual about to engage in an activity involving sickness-inducing motion, the method comprising: determining an effective dose of tradipitant for the individual, wherein the effective dose is a first dose if the individual is Hispanic, and is a second dose if the individual is non-Hispanic; and administering the effective dose of tradipitant to the individual, prior to the commencement of the activity, whereby the effective dose is effective to prevent motion sickness or at least one symptom of motion sickness in the individual.

Embodiment 42. The method of embodiment 41, wherein the second dose is larger than the first dose.

Embodiment 43. The method of embodiment 41 or 42, wherein the first dose is 100-400 mg.

Embodiment 44. The method of embodiment 43, wherein the first dose is 100-300 mg.

Embodiment 45. The method of embodiment 44, wherein the first dose is 100-200 mg.

Embodiment 46. The method of embodiment 45, wherein the first dose is about 170 mg.

Embodiment 47. The method of embodiment 46, wherein the first dose is 170 mg.

Embodiment 48. The method of any one of embodiments 43-47, wherein the second dose is about 150 mg to about 600 mg.

Embodiment 49. The method of embodiment 48, wherein the second dose is about 150 mg to about 450 mg.

Embodiment 50. The method of embodiment 49, wherein the second dose is about 150 to about 300 mg.

Embodiment 51. The method of embodiment 50, wherein the second dose is about 255 mg.

Embodiment 52. The method of embodiment 51, wherein the second dose is 255 mg.

Embodiment 53. The method of embodiment 41 or 42, wherein the second dose is 100-400 mg.

Embodiment 54. The method of embodiment 53, wherein the second dose is 100-300 mg.

Embodiment 55. The method of embodiment 54, wherein the second dose is 100-200 mg.

Embodiment 56. The method of embodiment 55, wherein the second dose is about 170 mg.

Embodiment 57. The method of embodiment 56, wherein the second dose is 170 mg.

Embodiment 58. The method of any one of embodiments 53-57, wherein the first dose is about 85 mg.

Embodiment 59. The method of embodiment 58, wherein the first dose is 85 mg.

Embodiment 60. The method of any one of embodiments 41-59, wherein the administering further comprises orally administering the tradipitant.

Embodiment 61. The method of embodiment 60, wherein the tradipitant is orally administered in a solid immediate release form comprising tradipitant and one or more pharmaceutically acceptable excipients.

Embodiment 62. The method of any one of embodiments 41-61, wherein the at least one symptom is nausea, dizziness, headache, fullness, or disorientation.

Embodiment 63. The method of any one of embodiments 41-61, wherein the at least one symptom is vomiting.

Embodiment 64. Tradipitant for use in any of the preceding methods of treatment or improvements.

Embodiment 65. A pharmaceutical composition comprising tradipitant for use in any of the preceding methods or improvements.

Embodiment 66. Tradipitant for use in the manufacture of a pharmaceutical composition comprising tradipitant for use in any of the preceding methods or improvements.

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. An improvement in a method of treating an individual about to engage in an activity involving sickness-inducing motion, the improvement comprising:

selecting the individual for treatment based on an ethnicity of the individual, wherein the individual is Hispanic; and administering tradipitant to the individual, prior to the commencement of the activity, in an amount effective to prevent motion sickness or at least one symptom of motion sickness in the individual.

2. The improvement of claim 1, wherein the activity is vehicle travel, wherein the vehicle travel is via automobile, airplane, helicopter, boat, train, or bus.

3. The improvement of claim 2, wherein the administration occurs about 30 minutes prior to entering a vehicle.

4. The improvement of claim 2, wherein the administration occurs about 30 minutes prior to commencement of vehicle travel.

5. The improvement of claim 1, wherein the effective amount is 100-400 mg.

6. The improvement of claim 1, further comprising orally administering the effective amount of tradipitant in a solid immediate release form comprising the tradipitant and one or more pharmaceutically acceptable excipients.

7. The improvement of claim 1, wherein the at least one symptom is nausea, vomiting, dizziness, headache, fullness, or disorientation.

8. An improvement in a method of treating an individual with motion sickness or at least one symptom of motion sickness, comprising:

administering tradipitant to the individual at a dose effective to treat the motion sickness or the symptom thereof, wherein the dose effective to treat the motion sickness or the symptom thereof is determined based on an ethnicity of the individual, and wherein the dose is a first amount if the individual is Hispanic, and is a second amount if the individual is non-Hispanic.

9. The improvement of claim 8, wherein the second amount is larger than the first amount.

10. The improvement of claim 9, wherein the first amount is 100-400 mg, and the second amount is about 150 mg to about 600 mg.

11. The improvement of claim 9, wherein the first amount is about 85 mg, and the second amount is 100-400 mg.

12. The improvement of claim 8, wherein the administration further comprises oral administration of tradipitant in a solid immediate release form comprising the tradipitant and one or more pharmaceutically acceptable excipients.

13. The improvement of claim 8, wherein the at least one symptom is vomiting, nausea, dizziness, headache, fullness, or disorientation.

14. A method of treating an individual about to engage in an activity involving sickness-inducing motion, the method comprising:

determining an effective dose of tradipitant for the individual, wherein the effective dose is a first amount if the individual is Hispanic, and is a second amount dose if the individual is non-Hispanic; and administering the effective dose of tradipitant to the individual, prior to the commencement of the activity, whereby the effective dose is effective to prevent motion sickness or at least one symptom of motion sickness in the individual.

15. The method of claim 14, wherein the second amount dose is larger than the first amount.

16. The method of claim 15, wherein the first amount dose is 100-400 mg, and the second amount is about 150 mg to about 600 mg.

17. The method of claim 15, wherein the first amount dose is about 85 mg, and the second amount is 100-400 mg.

18. The method of claim 14, wherein the at least one symptom is vomiting, nausea, dizziness, headache, fullness, or disorientation.

19. The method of claim 14, wherein the administering further comprises orally administering the tradipitant in a solid immediate release form comprising tradipitant and one or more pharmaceutically acceptable excipients.

20. The method of claim 19, wherein the solid immediate release form comprises a capsule or a tablet.

* * * * *